United States Patent
Tanaka et al.

Patent Number: 5,827,176
Date of Patent: Oct. 27, 1998

[54] ENDOSCOPIC IMAGING SYSTEM WITH ROTATING PHOTOELECTRIC LINE SENSOR

[75] Inventors: Toshizumi Tanaka; Kazuhiro Yamanaka, both of Omiya, Japan

[73] Assignee: Fuji Photo Optical Co., Ltd., Omiya, Japan

[21] Appl. No.: 797,119

[22] Filed: Feb. 10, 1997

[30] Foreign Application Priority Data

Feb. 13, 1996 [JP] Japan .................. 8-048398

[51] Int. Cl.⁶ ........................................ A61B 1/05
[52] U.S. Cl. .................. 600/109; 600/129; 600/160; 600/170
[58] Field of Search ................. 600/101, 109, 600/129, 160, 170; 348/65, 71, 82–85, 36, 37

[56] References Cited

U.S. PATENT DOCUMENTS 4,532,544 7/1985 Federau ........................... 348/65

Primary Examiner—John P. Leubecker
Attorney, Agent, or Firm—Oblon, Spivak, McClelland, Maier & Neustadt, P.C.

[57] ABSTRACT

An endoscopic imaging system for producing a flatly deployed expansion image of a tubular body cavity. The endoscopic imaging system essentially includes a photoelectric line sensor rotatably mounted on a distal end portion of an endoscopic insertion instrument for picking up a series of slit images around inner periphery of a tubular intracavitary wall sequentially at predetermined angular positions within an axial range commensurate with axial length of the line sensor; and an expansion image generating means arranged to produce a frame of picture signals for a flatly deployed expansion image of the tubular intracavitary wall from picture signals of slit images sequentially received from the image sensor.

5 Claims, 4 Drawing Sheets

ENDOSCOPIC IMAGING SYSTEM WITH ROTATING PHOTOELECTRIC LINE SENSOR

BACKGROUND OF THE INVENTION

1. Field of the Art

This invention relates to an endoscopic imaging system for use with an insertion instrument of endoscope, and more particularly to an endoscopic imaging system which is capable of producing, for display on a monitor screen, a flatly deployed expansion image of a tubular body cavity or of a tubular intracavitary wall under endoscopic observation.

2. Prior Art

An endoscope is largely constituted by a manipulating head assembly, a rod-like insertion instrument extended out on the front side of the manipulating head assembly for introduction into a body cavity or an intracavitary region of interest, and a universal cable led out on the rear side of the manipulating head assembly to connect the endoscope to other components of an endoscopic observation system. Mounted on distal end portions of the insertion instrument are illumination and endoscopic observation means as well known in the art. For illuminating a body cavity region under observation, a light guide is extended through the insertion instrument to project illumination light rays through an illumination window at the distal end of the insertion instrument.

The endoscopic observation means is arranged differently depending upon the type of endoscope, which can be an optical type or an electronic type. In the case of an optical endoscope, the endoscopic observation means normally includes an objective lens which is fitted in an observation window at the distal end of an insertion instrument, and a solid-state image sensor device which is positioned at the focus of the objective lens. Signal lines to and from the solid-state image sensor are passed through the insertion instrument and led out of the manipulating head assembly together with the light guide to form part of the above-mentioned universal cable. At the proximal end of the universal cable, the light guide and signal lines are provided with connectors for connection to an illumination light source and an image signal processor, respectively.

With an electronic endoscope of this sort, signals of picture images which are obtained through the solid-state image sensor are transferred to the signal processor and thereby processed into video signals to display, on a viewing screen of a monitor, video images of an intracavitary region under observation on real time basis. The video images displayed on a monitor screen have a view field in a different direction depending upon the positions of the illumination and observation windows on the insertion instrument. In the case of a straight or forward view endoscope with illumination and observation windows opened forward in the axial direction at the distal end of an insertion instrument, it has a view field in a direction straightforward of the distal end of the insertion instrument. In the case of a side view endoscope with illumination and observation windows opened on a lateral side of a distal end portion of an insertion instrument, it has a view field in a sideward direction perpendicularly to the longitudinal axis of the insertion instrument. Further, there are oblique view endoscopes with illumination and observation windows opened in an oblique direction intermediate between the straightforward and sideward directions to provide an oblique view field for certain endoscopic observation.

In any case, the view field of endoscopic observation is limited by the view field of the objective lens which is fitted in the observation window. On the other hand, body cavities to be examined by endoscopes have great varieties in shape and breadth including relatively broad cavities such as stomach or other organs, digestive tracts, duodenums, large intestines and so forth. For example, in the examination of a tubular intracavitary wall, the straight view endoscope provides a depthwise perspective view of intracavitary wall surfaces, that is to say, a sideways view of inner peripheral surfaces of the tubular intracavitary wall in the axial direction from a point immediately on the front side of an endoscopic observation window. On the other hand, the side view endoscope provides a front view of a virtually flat intracavitary wall surface portion in a particular locality around its inner periphery taken from a face-to-face position.

In endoscopically examining and diagnosing intracavitary wall tissues within a tubular body cavity, it is often found more advantageous to use a side view endoscope which permits to view a particular region of an intracavitary wall directly from a face-to-face position, rather than using a straight view endoscope which can pick up only sideways or depthwise perspective images of a body cavity. However, in the case of an insertion instrument with a side view observation window, which is designed to capture images of a certain locality of a tubular intracavitary wall, it is difficult to diagnose conditions all around the entire inner periphery of the intracavitary wall which might be infected with a disease over broad areas. On the other hand, in the case of an insertion instrument with a straight view observation window, it is possible to examine the entire inner periphery of an intracavitary wall portion as long as it is at a relatively short distance from the observation window, but difficulties are experienced in gripping conditions in broad areas of intracavitary wall surfaces from sideways perspective images which are displayed on a monitor screen.

SUMMARY OF THE INVENTION

It is an object of the present invention to provide an endoscopic imaging system which can produce a flatly deployed expansion image of a tubular body cavity for display on a monitor screen.

It is another object of the present invention to provide an endoscopic imaging system which can produce a flatly deployed expansion image of a tubular body cavity or tubular intracavitary wall in such a way as to bring to view ups and downs on the intracavitary wall surfaces in a clearly recognizable state.

In order to achieve the above-stated objectives, the present invention provides an endoscopic imaging system for producing a flatly deployed video image of a tubular body cavity. The imaging system is basically constituted by a photoelectric image sensor means which is rotatably mounted on a distal end portion of an endoscopic insertion instrument for picking up a series of slit images around entire inner periphery of a tubular intracavitary wall sequentially at predetermined angular intervals and within an axial range of the image sensor, and an expansion image generator which is connected to the image sensor means for generating, for display on a monitor screen, a flatly deployed image of the tubular intracavitary wall on the basis of picture signals of slit images, sequentially received from the image sensor means.

According to the present invention, in order to capture the entire inner periphery of a tubular intracavitary wall in the view field of endoscopic observation, the imaging system is arranged to generate and display on a monitor screen an expansion image which shows the tubular intracavitary wall in a flatly deployed state. From a flatly deployed expansion image of an intracavitary wall displayed on a monitor screen, the operator can clearly grip the dimensions of disease-affected regions even in case the affected regions extend or scatters substantially around the entire inner periphery of the intracavitary wall. Besides, in consideration of the fact that in most cases intracavitary wall surfaces have complicate shapes rather than a simple and smooth shape, an expansion image which shows a tubular intracavitary wall in a flatly deployed state can be of great help to the operator in getting the whole picture of conditions of complicate intracavitary walls including conditions even on those surface areas which would otherwise be overlooked due to complicacy in shape.

In the case of an electronic endoscope incorporating a photoelectric image sensor means thereby to convert an optical image into electrical signals through photoelectric conversion, it is possible to generate and display on a monitor screen a flatly deployed expansion image of a tubular intracavitary wall, by processing electrical picture signals from the image sensor means. For this purpose, however, the photoelectric image sensor means needs to be arranged have the entire inner periphery of a tubular intracavitary wall in its view field. In this regard, arrangements can be made to take the entire inner periphery of a tubular intracavitary wall either by way of one continuous view or by way of a series of segmental views which are shifted progressively along the inner periphery of the tubular intracavitary wall. Therefore, for capturing an image of the entire inner periphery of a tubular intracavitary wall, there may be employed either a line sensor having a large number of photoelectric elements in a row or an area sensor having a multitude of photoelectric elements arrayed in X- and Y-directions. Of these two types of image sensors, the line sensor is more advantageous in consideration of simplicity in construction.

In the case of a line sensor, it is mounted rotatably on a distal end portion of an endoscopic insertion instrument, with the respective photoelectric sensor elements of the line sensor aligned in a row in the axial direction of the insertion instrument, that is to say, in the axial direction of a tubular body cavity to be examined by the endoscopic insertion instrument. The line sensor is mounted on a rotational shaft which is coupled with a rotational drive means for rotation approximately about the longitudinal axis of the insertion instrument. While the rotational shaft is put in rotation in such a way as to pan or scan the line sensor along the inner periphery of a tubular intracavitary wall, a slit picture image of a predetermined width is captured through the line sensor sequentially at predetermined angular positions during one rotation or during a rotation through 360° to produce a series of slit picture images of all intracavitary wall surfaces around the distal end portion of the insertion instrument in an axial range commensurate with the axial length of the line sensor.

While in rotation, the angular position of the line sensor is constantly detected by an encoder or other rotational angle detection means to obtain position signals for the respective slit picture images in the horizontal direction (or in the vertical direction) and a signal of an original image scanning position. Along with signals of slit picture images which are sequentially output from the line sensor, the angular position signals are fed to an expansion image generator to produce frame picture signals for a flatly deployed expansion image of tubular intracavitary wails around the distal end portion of the endoscopic insertion instrument.

For picking up images in a dark place like body cavity, it is necessary to illuminate the object of endoscopic observation, in this case, the entire inner periphery of the intracavitary wall to be scanned by the rotating line sensor. Illumination light is transmitted to the distal end of the endoscopic insertion instrument from an illumination light source through a light guide which is axially passed through the endoscopic insertion instrument. According to the invention, in order to illuminate the entire inner periphery of the intracavitary wall with light rays axially projected from the light guide, the fore light emitting end of the light guide is diverged into an annular ring-like shape, and a conical reflector mirror with a substantially conical light reflecting surface is located in front of the light emitting end of the light guide thereby to reflect the illumination light rays uniformly in radial directions around the distal end portion of the endoscopic insertion instrument, instead of bending the light emitting end of the light guide in radial directions.

BRIEF DESCRIPTION OF THE DRAWINGS

The above and other objects, features and advantages of the invention will become apparent from the following description taken in conjunction with the accompanying drawings which show by way of example preferred embodiments of the invention and in which.

DESCRIPTION OF PREFERRED EMBODIMENTS

Hereafter, the invention is described more particularly by way of its preferred embodiments with reference to the accompanying drawings. In the following preferred embodiments of the invention, a line sensor is employed as the most expedient form of the image sensor means according to the invention.

Figure 1:
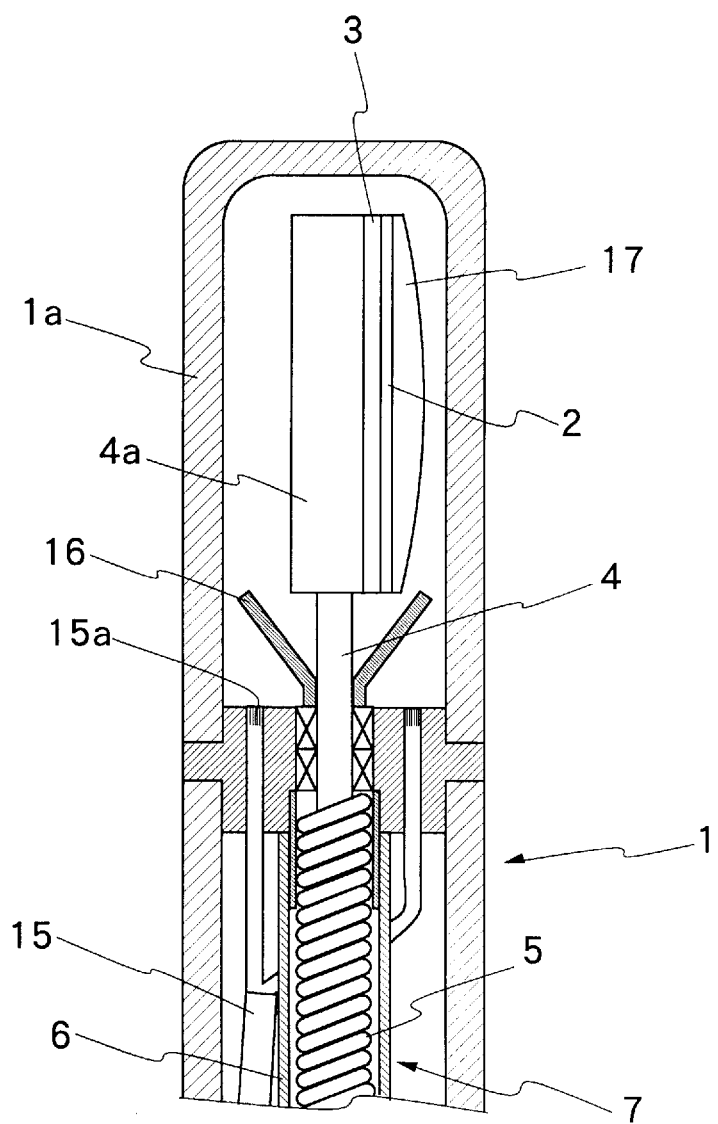
FIG. 1 is a schematic sectional view of an embodiment of an image sensor means according to the invention, incorporated into an endoscopic insertion instrument.

Referring first to FIG. 1, there is shown a distal end portion of an endoscopic insertion instrument, incorporating an image sensor means according to the invention. More specifically, in FIG. 1, indicated at 1 is an endoscopic insertion instrument, which is fitted with a rigid cylindrical end housing or casing 1a of a predetermined length at its distal end. The end casing 1a is formed of transparent synthetic resin material to provide a circular clear observation window all around. Provided within the transparent end casing 1a is a line sensor 2 consisting of a row of a large number of photoelectric sensors in the axial direction of the end casing 1a. The line sensor 2 is mounted on a substrate 3 which is in turn securely fixed on a support portion 4a at the fore end of an axial rotational shaft 4 extending into the end casing 1a substantially along the center axis of the latter. Accordingly, when the rotational shaft 4 is turned about its axis, the line sensor 2 is turned around within the clear end casing 1a in such a way as to scan around the end casing 1a.

At the time of introducing the endoscopic insertion instrument 1 into a body cavity of interest, it may come across a narrow constricted portion or portions along the path of insertion, so that it is desirable for the insertion instrument 1 to be as small as possible in diameter and as short as possible in length of the rigid end casing 1a from the standpoint of lessening pains on the part of patient and ensuring smooth insertion of the instrument 1. For these reasons, it is undesirable for the end casing 1a to accommodate a motor or similar rotational drive means which would result in increased balkiness of the end casing 1a. Therefore, the rotational shaft 4 needs to be driven from a remote drive source through a rotation transmission means which can transmit rotations accurately and securely to the rotational shaft 4 and which has sufficient flexibility to permit flexure of the insertion instrument 1. In order to meet these requirements, it has been the usual practice to employ a flexible transmission shaft 5 which consists of tightly wound metal wire coils. The flexible shaft 5 is in the form of a hollow tube, internally providing a passage for a signal cable which is connected to the line sensor 2. The flexible shaft 5 is assembled with the signal cable to constitute a control cable assembly 7, and fitted in a flexible sleeve 6 which is fixed at the opposite ends thereof.

Figure 2:
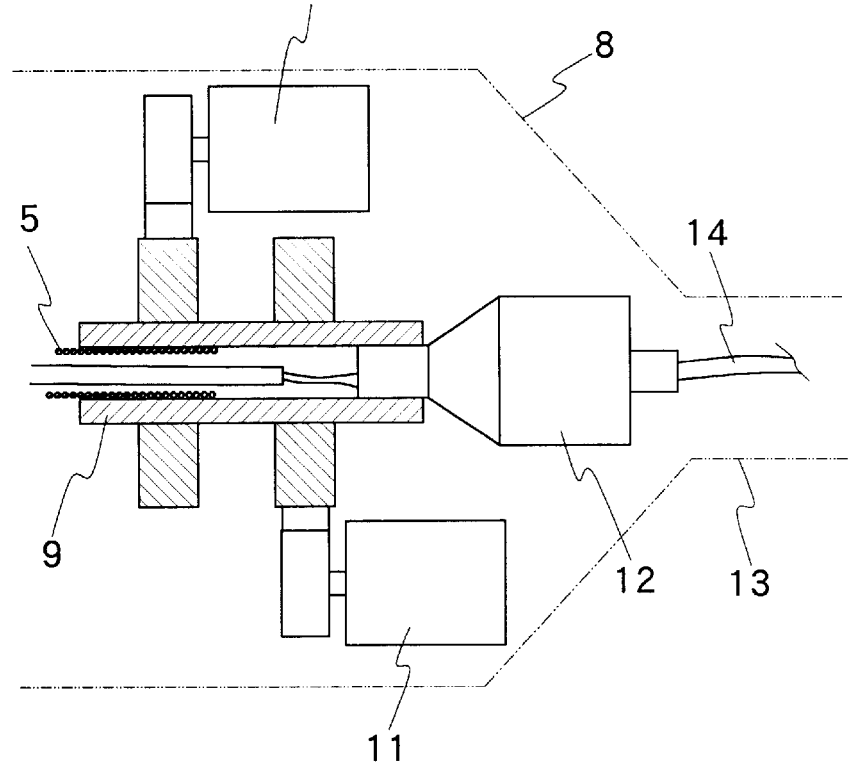
FIG. 2 is a schematic illustration of a rotational drive mechanism for the image sensor means.

As seen in FIG. 2, the control cable assembly 7 is extended through the endoscopic insertion rod 1 and into a manipulating head assembly 8 of the endoscopic insertion instrument. At the proximal end of the insertion rod 1 on the side of the manipulating head 8, the flexible shaft 5 is led out of the flexible sleeve 6 and connected to a drive shaft 9. The drive shaft 9 is coupled with a rotational drive source such as an electric motor 10 or the like through rotation transmission means such as transmission belt or gears (a transmission belt is shown in the drawing). The drive gear 9 is also coupled with an encoder 11 through a similar rotation transmission means. The signal cable which is passed through the flexible shaft 5 is connected to a rear signal cable 14 in the universal cable assembly 13 which is led out of the manipulating head 8 of the insertion instrument, through a slip ring, rotary connector or other relay member 12 which is composed of a combination of rotatable and fixed parts.

The endoscope is provided with an illumination means for lighting up an intracavitary region under observation, including a light guide 15 which is passed through the insertion rod 1. The light guide 15 is constituted by a bundle of a large number of fine optical fibers, which are bundled together up to a halfway point of the insertion rod 1 and spread into an annular form in a fore end portion of the insertion rod 1 to provide an annular light emitting end 15a. Illumination light rays which are projected axially forward from the light emitting end 15a of the light guide 15 are turned approximately through 90° by a conical reflector mirror 16 which is located between the line sensor 2 on the rotational shaft 4 and the light emitting end 15a of the light guide 15. The conical reflector mirror 16 is provided with an inclined reflecting surface which is disposed approximately at 45° or at a smaller angle with the axis of the end casing 1a of the insertion rod 1. Illumination light rays are suitably diffused either by providing a diffuser lens on the front side of the light emitting end 15a of the light guide 15 or by forming the light reflecting surface of the reflector mirror 16 into a concave shape. By diffusing illumination light rays in this manner, a tubular body cavity to be scanned by the rotating line sensor in an endoscopic observation can be uniformly illuminated substantially with the same level of illumination light on all the intracavitary wall surfaces which surround the distal end casing 1a of the insertion instrument.

With the arrangements just described, illumination light rays from the light guide 15 are reflected by the conical reflector mirror 16 to illuminate all the intracavitary wall surfaces around the end casing 1a of the insertion rod 1, and in the illuminated state the motor 10 is actuated to drive the rotational shaft 4 through the flexible transmission shaft 5. While the rotational shaft 4 is put in rotation, signal charges accumulated in the respective photoelectric sensor elements of the line sensor 2 are sequentially read out and transferred to a signal processor to acquire picture signals of a series of slit picture images around the inner periphery of a tubular intracavitary wall within an axial range of the line sensor. A series of slit picture images, resulting from the scanning operation by the line sensor, are successively aligned in one plane to obtain a flatly deployed expansion image of the scanned intracavitary wall. In this regard, in order to improve the resolution of the expansion image, the individual slit picture images which make up the flat expansion image should have as small a width as possible. To this end, a conversion lens 7 is fitted on a light receiving surface of the line sensor 2. On one revolution of the line sensor 2, a series of narrow slit picture images are sequentially picked up through 360° along the inner periphery of a tubular body cavity, for instance, at angular intervals of 0.5° to generate picture signals for one frame of an expansion image for displaying the entire inner periphery of the body cavity in a flatly expanded state on a monitor screen.

Figure 3:
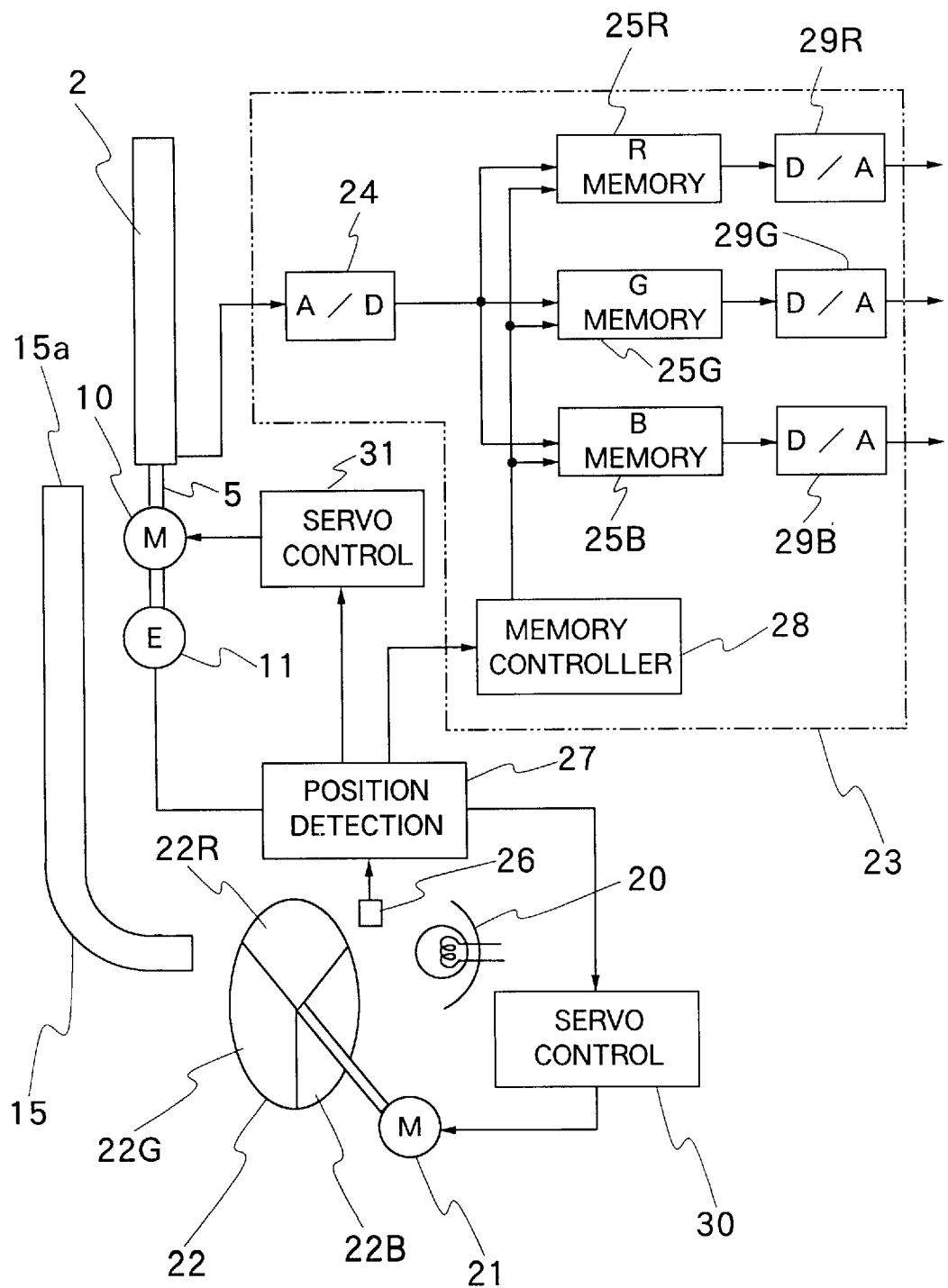
FIG. 3 is a circuit diagram showing an example of expansion image generator.

Shown in FIG. 3 is an endoscopic imaging system for producing color expansion images of tubular body cavities.

More specifically, shown in FIG. 3 is an endoscopic imaging system which is arranged to produce RGB picture signals on every three revolutions of the line sensor 2. In this case, light rays from an illumination light source 20 are passed sequentially through RGB filter sectors of a color wheel 22 which is rotationally driven by a motor 21. By rotation of the color wheel 22, illumination light rays of RGB wavelengths are sequentially projected into a body cavity under observation through the light guide 15. The line sensor 2 is driven by the motor 10 to complete one revolution in each one of RGB illumination periods, while accumulated signal charges are sequentially read out from the line sensor 2, for example, at angular intervals of 0.5° to obtain RGB slit picture image signals for intracavitary wall areas within the axial scan range of the line sensor 2. The resulting RGB slit picture image signals are sequentially transferred to an expansion image generator 23.

The line sensor 2 which plays the double role of light reception and signal charge transfer is divided into a light receiving section and a charge transfer section which is shielded to incident light. Accumulated signal charges are shifted from the light receiving section to the signal transfer section at predetermined angular intervals during rotation of the line sensor 2 for transfer to the expansion image generator 23. In case the rotational shaft 4 is driven at a low speed, the signal accumulation periods of the light receiving section can be limited to a suitable time length by the use of an electronic shutter.

While a red filter sector 22R of the color filter wheel 21 is brought into and passed across a light path from the source lamp 20 to the light guide 15 by operation of the motor 21, the light sensor 2 completes one rotation and at this time signals of red slit picture images are transferred to the expansion image generator 23 at predetermined angular intervals to generate one frame of red picture signals. The line sensor 2 completes another rotation when and while a green filter sector 22G is passed across the illumination light path, picking up green slit picture images in a similar manner for generating one frame of green picture signals. Then, while a blue filter sector 22B of the color filter wheel 22 is passed across the illumination light path to irradiate light rays of blue wavelength, the line sensor 2 completes another rotation to generate one frame of blue picture signals. These RGB picture signals are transferred to a video signal processor and thereby processed into a color video image for display on a monitor screen.

More particularly, RGB picture signals which are read out by driving the line sensor 2 are converted into digital signals through A/D converter 24 of the image signal processor 23 and stored in RGB frame memories 25R, 25G and 25B. In this instance, in order to convert the signals from the line sensor 2 into frame signals of the respective colors, it is necessary to detect the RGB irradiation periods as well as the angular position of the line sensor 2. In the particular embodiment shown in the drawings, a sensor 26 is located in face to face relation with the color wheel 22 for detecting the RGB irradiation periods by way of the angular position of the color wheel 22. On the other hand, output signals of the encoder 11, indicative of the rotational angle of the flexible transmission shaft 5 which is driven by the motor 10, are fed to a position detector circuit 27 thereby to determine the angular position of the line sensor 2. These detection signals are transferred to a memory controller 28 which produces control signals for assignment of addresses to RGB picture data to be stored in the memories 25R, 25G and 25B. As a result, a large number of slit picture images of each color are converted into frame signals, base signals for a color expansion image to be displayed on a monitor screen. Namely, the frame picture signals of the respective colors are converted into analog signals through D/A converters 29R, 29G and 29B and output to a video processor to produce a color video image by signal processing operations well known in the art.

In this instance, since the color wheel 22 is rotated by the motor 21 independently of the line sensor 2 which is driven by the motor 10, signals of the color wheel angle sensor 26 are constantly compared with predetermined reference position signals (indicative of initial positions of color picture signals to be stored in the RGB memories 25R, 25G and 25B) which periodically occur in the rotational angle detection signals of the encoder 11, adjusting the operation of the motor 21 through a servo circuit 30 to match the rotation of the color wheel 22 with that of the line sensor 2. Further, for the purpose of precluding irregularities in rotational speed of the line sensor 2, the rotational angle detection signals of the encoder 11 are also fed to a servo circuit 31 which controls the operation of the motor 10.

With the arrangements just described, while rotating the line sensor 2 by the sensor drive motor 10, accumulated signal charges are read out therefrom at predetermined angular intervals and sequentially transferred to the image processor 23 to produce RGB frame picture signals. Namely, signals of slit picture images of each colors, which are read out on every one rotation of the line sensor 2, are converted into a set of frame signals and sequentially transferred to the image processor at which the RGB frame signals are processed into simultaneous color image signals for display on a monitor screen. As mentioned hereinbefore, the color image on the monitor screen is an expansion image which shows a tubular intracavitary wall in a flatly deployed state to permit the operator to grip clearly and precisely the whole picture of the intracavitary wall under endoscopic observation.

Figure 5:
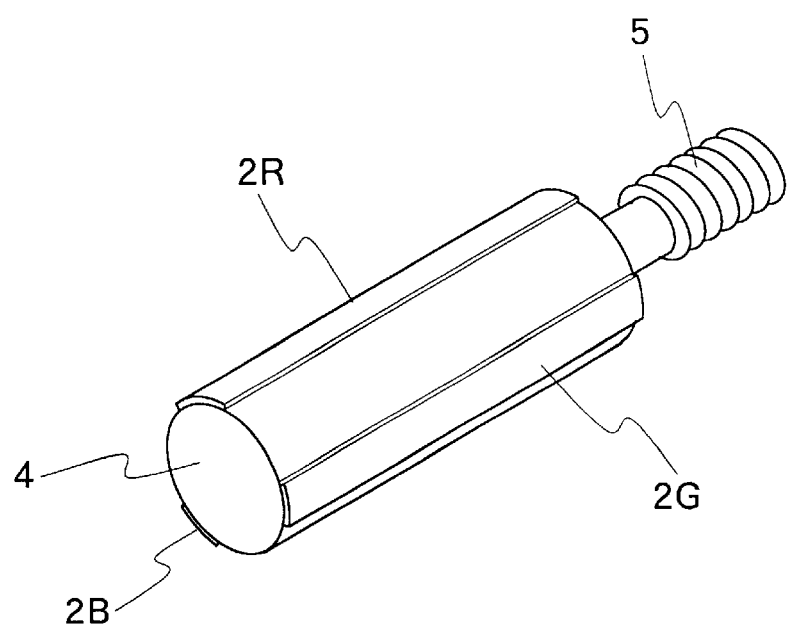
FIG. 5 is a schematic perspective view of a modification of the image sensor means according to the invention.
Figure 4:
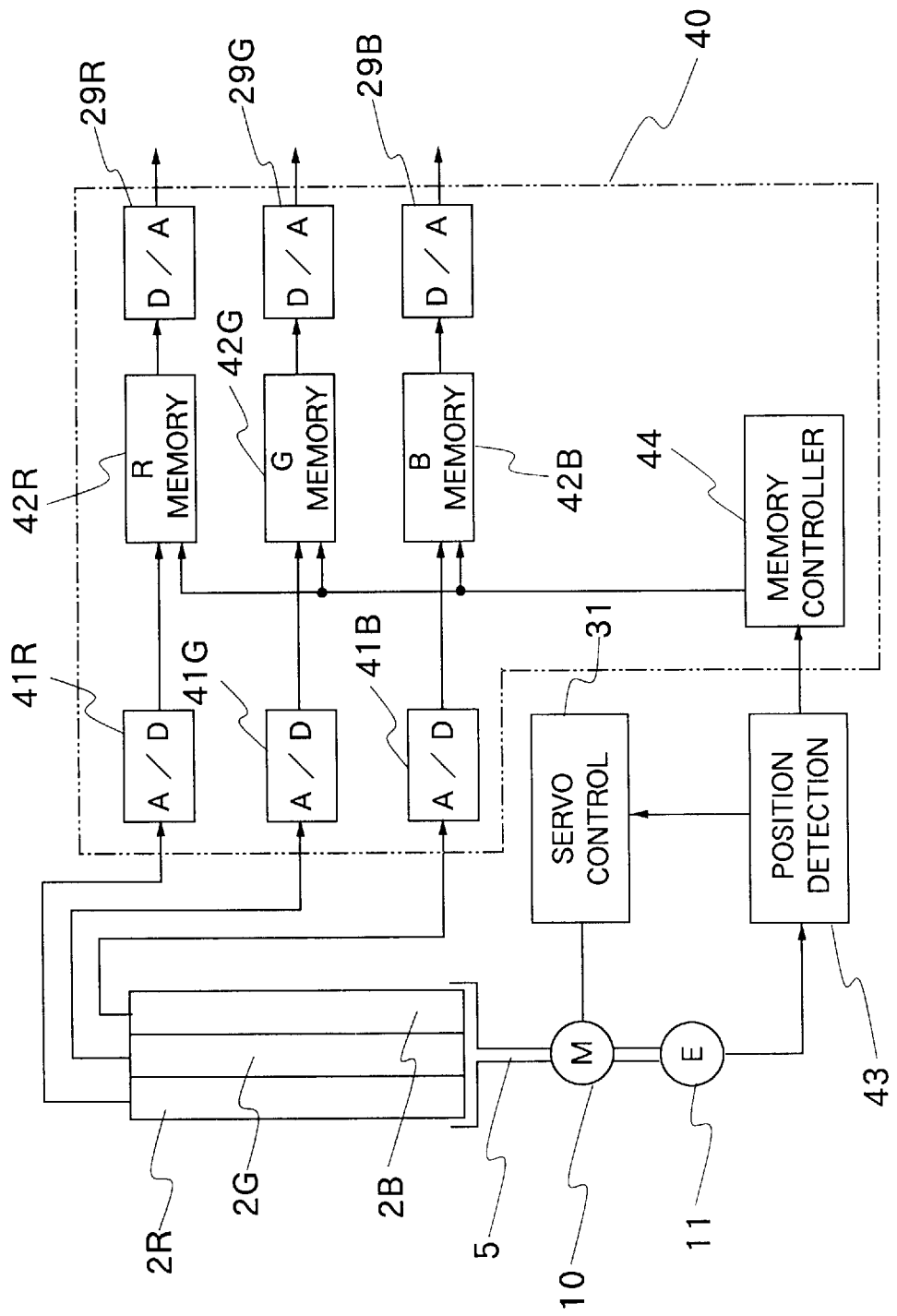
FIG. 4 is a circuit diagram showing an example of color expansion image generator.

Referring now to FIG. 4, there is shown another endoscopic imaging system for producing in color a flatly deployed expansion image of a tubular intracavitary wall. As shown particularly in FIG. 5, this system employs three line sensors 2R, 2G and 2B parallelly in equidistantly spaced positions around the circumference of the rotational shaft 4. Of the three line sensors 2R, 2G and 2B, a filter which is transmissive of red wavelength alone is mounted on a light receiving surface of the first line sensor 2R, a filter which is transmissive of green wavelength alone is similarly mounted on the second line sensor 2G, a filter which is transmissive of blue wavelength alone is mounted on the third line sensor 2B. These first to third line sensors 2R, 2G and 2B are located in equidistant positions around the rotational shaft 4 with a phase shift of 120° from each other.

In this embodiment, with the arrangements as described above, a white light lamp can be used for the illumination light source. Besides, all of RGB frame signals can be obtained during one and single rotation of the rotational shaft 4. In this instance, slit image signals from the RGB line sensors 2R, 2G and 2B are separately fed to an expansion image generator 40 and stored in RGB frame memories 42R, 42G and 42B after conversion into digital signals through A/D converters 41R, 41G and 41B, respectively. The provision of three A/D converters 41R, 41G and 41B makes it possible to read in RGB slit image signals simultaneously. However, slit image signals of the respective colors can be read in sequentially through a single A/D converter in case the charge signal transfer speed is high enough relative to the rotational speed of the line sensors. On the other hand, for storing slit image signals of the respective colors in the memories 42R, 42G and 42B, the anglar positions of the line sensors 2R, 2G and 2B are detected by a position detector circuit 43 on the basis of the rotational angle of the drive shaft 4 as indicated by signals from the encoder 11, and the resulting angular position signals are supplied to a memory controller 44 thereby to assign addresses to picture signals to be stored in the memories 42R, 42G and 42B. In this instance, since the three line sensors 2R, 2G and 2B are located with a phase shift of 120° from one another, it becomes necessary to bring the picture signals of RGB frames in phase with each other by delaying G and B frame signals relative to R frame signals by 120° and 240° respectively.

Thus, in this embodiment, signals of slit picture images from the respective line sensors are converted into RGB frame signals, which are then processed into simultaneous color video signals by a video signal processor to display on a monitor screen a color expansion image of a tubular body cavity in a flatly deployed state.

What is claimed is:

1. An endoscopic imaging system for producing a flatly deployed expansion image of a tubular body cavity, comprising:

a photoelectric line sensor rotatably mounted within a distal end portion and aligned in a row with an axial direction of an endoscopic insertion instrument for picking up a series of slit images around inner periphery of a generally tubular intracavitary wall sequentially at predetermined angular positions and within an axial range of said line sensor; and an expansion image generating means arranged to produce a frame of picture signals for a flatly deployed expansion image of said intracavitary wall on the basis of picture signals of said series of slit images sequentially received from said image sensor.

2. An endoscopic imaging system, comprising;

a photoelectric line sensor supported on a rotational shaft within a distal end portion of an endoscopic insertion instrument and constituted by a large number of photoelectric sensor elements aligned in an a row in axial direction of said endoscopic insertion instrument, said line sensor being rotated by said rotatable shaft to pick up a series of slit images around inner periphery of said intracavitary wall sequentially at predetermined angular intervals within an axial range of said line sensor;

a rotational drive means coupled with said rotational shaft for rotating said line sensor substantially about the longitudinal axis of said endoscopic insertion instrument;

a rotational angle detection means for detecting angular positions of said rotatable member while in rotation; and an expansion image generating means arranged to produce a frame of picture signals for a flatly deployed expansion image of said intracavitary wall on the basis of picture signals of slit images sequentially received from said line sensor at predetermined angular positions and angular position signals from said rotational angle detection means.

3. An endoscopic imaging system as defined in claim 2, further comprising: an illumination light guide having an annular light emitting end to project illumination light rays in an annular pattern toward said distal end portion of said endoscopic insertion instrument; and a conical reflector mirror located between said line sensor and said annular light emitting end of said light guide.

4. An endoscopic imaging system as defined in claim 3, wherein said light guide is associated with a color wheel to project illumination light rays of red, green and blue wavelengths cyclically from said light emitting end.

5. An endoscopic imaging system as defined in claim 3, wherein said light guide is arranged to project white light, and said photoelectric line sensor is constituted by three axial line sensors located in equidistant positions around the circumference of said rotatable member and fitted with color filters transmissive of light rays of red, green and blue wavelengths, respectively.

\* \* \* \* \*